(12) United States Patent
Beebe et al.

(10) Patent No.: US 10,286,419 B2
(45) Date of Patent: May 14, 2019

(54) PENCIL GUN

(71) Applicant: Fishman Corporation, Hopkinton, MA (US)

(72) Inventors: W. Scott Beebe, Berkley, MA (US); David Thomas, Milford, MA (US)

(73) Assignee: Fishman Corporation, Hopkinton, MA (US)

( * ) Notice: Subject to any disclaimer, the term of this patent is extended or adjusted under 35 U.S.C. 154(b) by 0 days.

(21) Appl. No.: 15/821,241

(22) Filed: Nov. 22, 2017

(65) Prior Publication Data

US 2018/0154390 A1 Jun. 7, 2018

Related U.S. Application Data

(60) Provisional application No. 62/425,790, filed on Nov. 23, 2016.

(51) Int. Cl.
| | | |
|---|---|---|
| *B05C 17/005* | (2006.01) | |
| *B05C 17/01* | (2006.01) | |
| *A61M 5/20* | (2006.01) | |
| *A61M 5/315* | (2006.01) | |

(52) U.S. Cl.
CPC ......... *B05C 17/00593* (2013.01); *A61M 5/20* (2013.01); *B05C 17/0116* (2013.01); *A61M 2005/2006* (2013.01); *A61M 2005/2026* (2013.01); *A61M 2005/31588* (2013.01)

(58) Field of Classification Search
CPC .................. B05C 17/0116; B05C 17/00593
USPC ............ 222/52, 63, 325–327, 333, 386, 390
See application file for complete search history.

(56) References Cited

U.S. PATENT DOCUMENTS

| | | | | |
|---|---|---|---|---|
| 3,623,474 A | * | 11/1971 | Heilman ................ | A61B 6/504 600/432 |
| 3,683,977 A | | 8/1972 | Crowe et al. | |
| 4,598,840 A | * | 7/1986 | Burg ....................... | G01N 1/38 222/135 |
| 5,022,556 A | * | 6/1991 | Dency ..................... | B05C 11/10 118/410 |
| 5,269,762 A | * | 12/1993 | Armbruster ............ | A61M 5/20 604/131 |
| 5,279,569 A | * | 1/1994 | Neer .................. | A61M 5/14546 222/327 |

(Continued)

FOREIGN PATENT DOCUMENTS

KR    20140076938 A    6/2014

OTHER PUBLICATIONS

International Search Report issued in Application Serial No. PCT/US2017/063064 dated Feb. 9, 2018.

*Primary Examiner* — Vishal Pancholi
(74) *Attorney, Agent, or Firm* — Mark H. Whittenberger; Holland & Knight LLP (57) ABSTRACT

Embodiments included herein are directed towards an apparatus that may be used to dispense a fluid. The apparatus may include a housing, wherein the housing includes a first end and a motor, wherein the first end is configured to be coupled to a syringe. The motor may be configured to be operatively connected to a drive tube, wherein at least a portion of the drive tube is configured to extend from and retract into an opening in the first end of the housing in response to the motor. One or more of the motor and the drive tube may be rotationally fixed to the housing. A first end of the drive tube may be configured to be coupled to a piston of the syringe.

16 Claims, 9 Drawing Sheets

(56) References Cited

U.S. PATENT DOCUMENTS

| | | | |
|---|---|---|---|
| 5,630,527 A | 5/1997 | Beebe et al. | |
| 5,868,710 A | 2/1999 | Battiato et al. | |
| 6,575,331 B1 | 6/2003 | Peeler et al. | |
| 6,682,601 B1 | 1/2004 | Beebe | |
| 7,334,706 B2 * | 2/2008 | Schroeder | B67D 1/0021 222/1 |
| 7,617,953 B2 * | 11/2009 | Tourigny | G01F 11/029 222/309 |
| 7,686,789 B2 * | 3/2010 | Nemoto | A61M 5/14546 604/131 |
| 8,777,063 B2 * | 7/2014 | Beebe | B05C 5/0208 222/181.3 |
| 2002/0016572 A1 | 2/2002 | Beebe | |
| 2013/0041346 A1 * | 2/2013 | Alon | A61M 5/20 604/506 |
| 2016/0107187 A1 | 4/2016 | Beebe | |

* cited by examiner

PENCIL GUN

RELATED APPLICATIONS

This application claims the benefit of U.S. Provisional Application No. 62/425,790 filed on 23 Nov. 2016, entitled Pencil Gun, the contents of which is incorporated by reference in its entirety.

BACKGROUND

Fluid dispensing systems may be used in conjunction with a variety of fluid sources. For example, certain systems may utilize fluid-filled syringes that may contain liquids, gels, liquid adhesives, etc. Fluid dispensing systems utilized to dispense fluid from these fluid-filled syringes may be configured in a variety of ways. For example, a fluid dispensing system may engage with a syringe to dispense the contents of the syringe in a controlled, precise manner.

SUMMARY

In one example implementation, an apparatus may include, but is not limited to a housing, wherein the housing may include a first end and a motor, wherein the first end may be configured to be coupled to a syringe. The motor may be configured to be operatively connected to a drive tube, wherein at least a portion of the drive tube may be configured to extend from and retract into an opening in the first end of the housing in response to the motor. One or more of the motor and the drive tube may be rotationally fixed to the housing. The first end of the drive tube may be configured to be coupled to a piston of the syringe.

One or more of the following example features may be included. The opening of the first end of the housing may include a wiper and the portion of the driver tube may be further configured to extend from and retract into the opening in the first end of the housing through the wiper. The apparatus may include a piston hub, wherein a first end of the piston hub may be configured to be coupled to the first end of the driver tube and a second end of the piston hub may be configured to be coupled to a piston of the syringe. The apparatus may include a retainer ring, wherein the retainer ring may be configured to receive a non-dispensing end of the syringe and may be further configured to be coupled to the first end of the housing. The apparatus may include a membrane switch, wherein the membrane switch may be configured to activate when the portion of the driver tube is fully retracted into the housing. One or more of the motor and the drive tube may be rotationally fixed to the housing with an anti-rotational device. The motor may be anchored within the housing. The motor may include a thrust coupling.

In another example implementation, a pencil gun may be used with a syringe. The syringe may have a cylinder with a first end and a second end, a piston assembly, an output at the first end and an opening for a shaft at the second end of the cylinder. The pencil gun may include a housing, wherein the housing may include a first end and a motor, an opening for a shaft at the first end, wherein the first end may be configured to be coupled to the second end of the syringe. The motor may be configured to be operatively connected to a drive tube, wherein at least a portion of the drive tube may be configured to extend from and retract into the opening in the first end of the housing in response to the motor. One or more of the motor and the drive tube may be rotationally fixed to the housing. The first end of the drive tube may be configured to be coupled to the piston assembly of the syringe.

One or more of the following example features may be included. The opening of the first end of the housing may include a wiper and the portion of the driver tube may be further configured to extend from and retract into the first end of the housing through the wiper. The pencil gun may include a piston hub, wherein a first end of the piston hub may be configured to be coupled to the first end of the driver tube and a second end of the piston hub may be configured to be coupled to a piston of the syringe. The pencil gun may include a retainer ring, wherein the retainer ring may be configured to receive a non-dispensing end of the syringe and may be further configured to be coupled to the first end of the housing. The pencil gun may include a membrane switch, wherein the membrane switch may be configured to activate when the portion of the driver tube is fully retracted into the housing. One or more of the motor and the drive tube may be rotationally fixed to the housing with an anti-rotational device. The motor may be anchored within the housing. The motor may include a thrust coupling.

The details of one or more example implementations are set forth in the accompanying drawings and the description below. Other possible example features and/or possible example advantages will become apparent from the description, the drawings, and the claims. Some implementations may not have those possible example features and/or possible example advantages, and such possible example features and/or possible example advantages may not necessarily be required of some implementations.

BRIEF DESCRIPTION OF THE DRAWINGS

The accompanying drawings, which are included to provide a further understanding of embodiments of the present disclosure and are incorporated in and constitute a part of this specification, illustrate embodiments of the present disclosure and together with the description serve to explain the principles of embodiments of the present disclosure.

Like reference symbols in the various drawings indicate like elements.

DETAILED DESCRIPTION

Existing fluid dispensing systems may suffer from one or more deficiencies. Fluid dispensing systems, particularly "pencil guns", may include magnetic components and/or may utilize magnetic connections between components. These magnetic components and/or connections (e.g., "magnetics") may destroy electronics and electronic chips and may also magnetize adjacent metals. Furthermore, magnetics may destroy the mix of filled assembly fluids such as solder paste and silver solder. In addition, conventional fluid dispensing systems may expose internal components to assembly fluids. Because these assembly fluids may include powerful adhesives, fluid dispensing systems may be damaged. Additionally, internal components of conventional fluid dispensing systems may be susceptible to moving and/or rotating during operation.

As will be discussed in greater detail below and referring also at least to FIGS. 1-6, the present disclosure may relate to a dispensing apparatus, and more particularly, a syringe-based positive displacement dispensing apparatus. Dispensing apparatus 100 may also be referred to as a "pencil gun". The housing 102 of dispensing apparatus 100 may also be referred to as a "gun shell". In some embodiments, dispensing apparatus 100 may be configured to be coupled to a syringe 104. In general, a syringe 104 may define a cylinder with a first end 106 and a second end 108, a piston assembly 110, an output at the first end of the cylinder (e.g., the "dispensing end") and an opening for a shaft at the second end of the cylinder (e.g., the "non-dispensing end"). In some embodiments, the second end 108 of syringe 104 may be coupled to dispensing apparatus 100 for dispensing the contents of the syringe.

Figure 2:
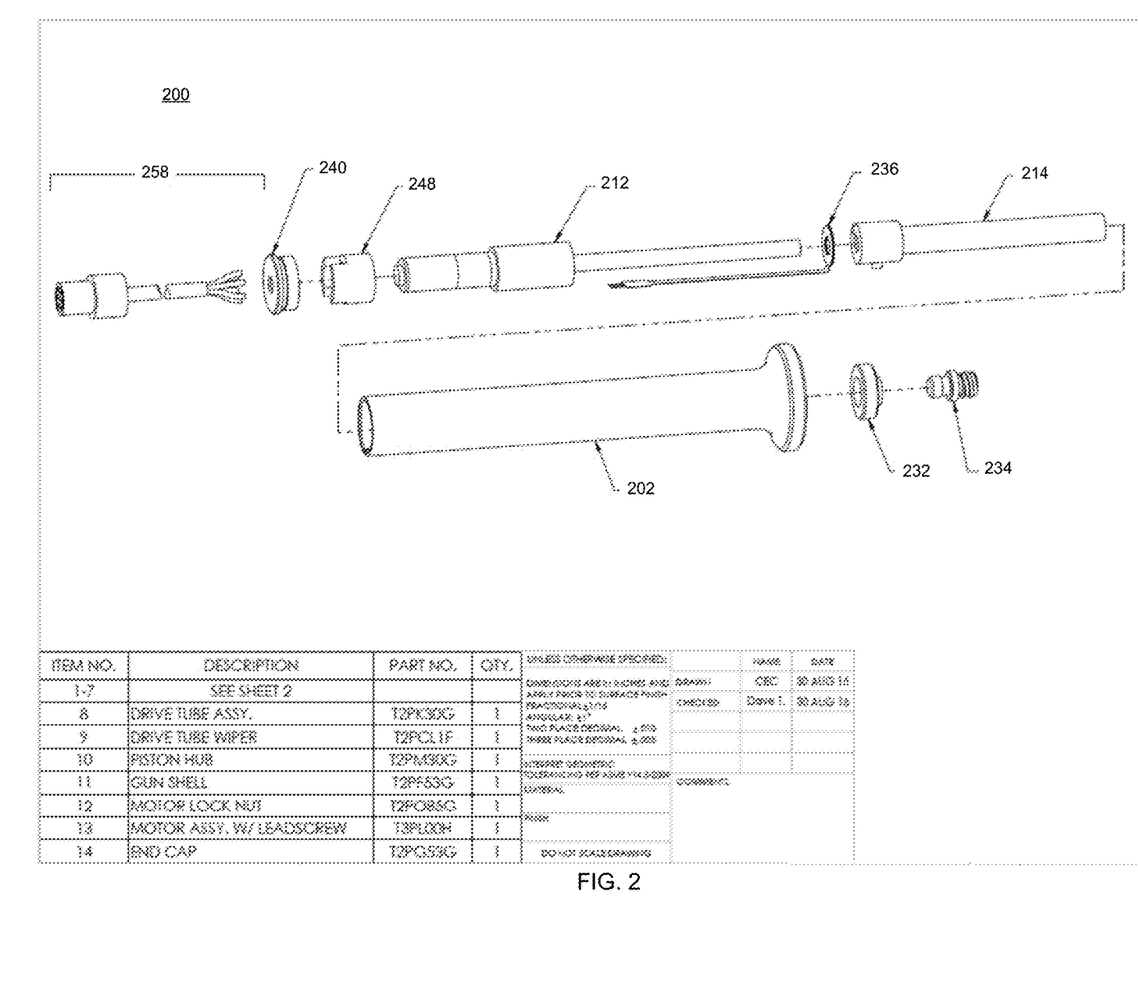
FIG. 2 is an example diagrammatic view of a dispensing apparatus according to one or more example implementations of the disclosure.

For example and referring also to FIG. 2, the dispensing apparatus 200 may utilize a motor assembly 212 to maneuver a drive tube assembly 214 in both forward and reverse motion. The drive tube assembly 214 may drive a piston assembly 110 within a syringe 104. Operations of the motor assembly 212 may sequentially advance and retract a drive tube assembly 214 relative to the syringe 104. Based upon this motion, the motor assembly 212 may sequentially create both a positive pressure and a negative pressure within the syringe 104 to result in the dispensing of contents from the syringe.

Figure 1:
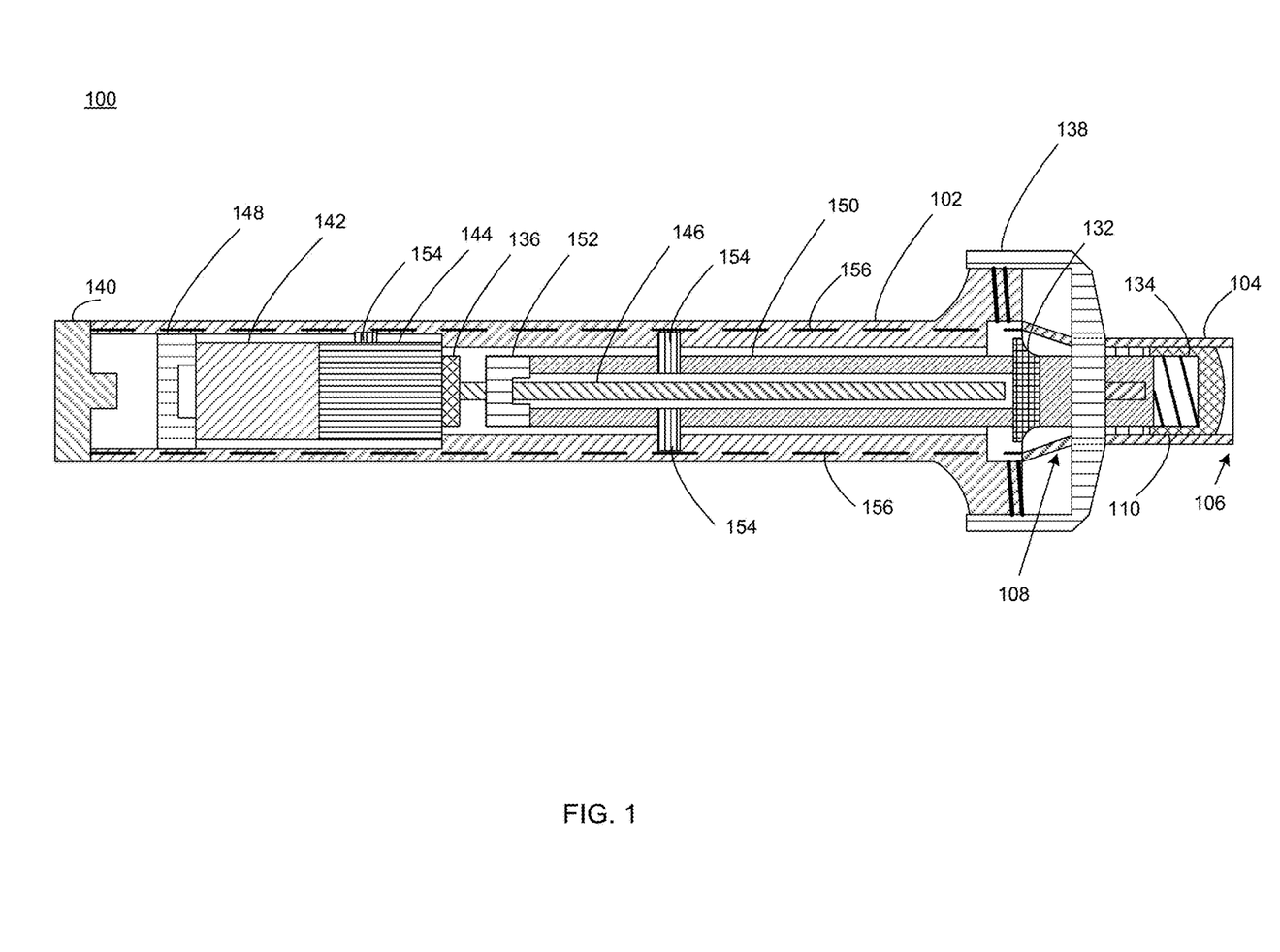
FIG. 1 is an example diagrammatic view of a dispensing apparatus according to one or more example implementations of the disclosure.

As will also be discussed in greater detail, in some implementations, the dispensing apparatus 100 may include a housing 102 and a motor assembly 212 carried by the housing 102. A power source (not shown), such as a battery or wired connection to a power outlet, may be disposed in electrical communication with motor assembly 212. In some embodiments, the power source may be connected to dispensing apparatus 100 via an electrical cable 258. The motor assembly 212, and/or components of the motor assembly, may maneuver a drive tube assembly 214, and/or components of the drive tube assembly, to engage with a piston assembly 110 of a syringe 104.

Figure 3:
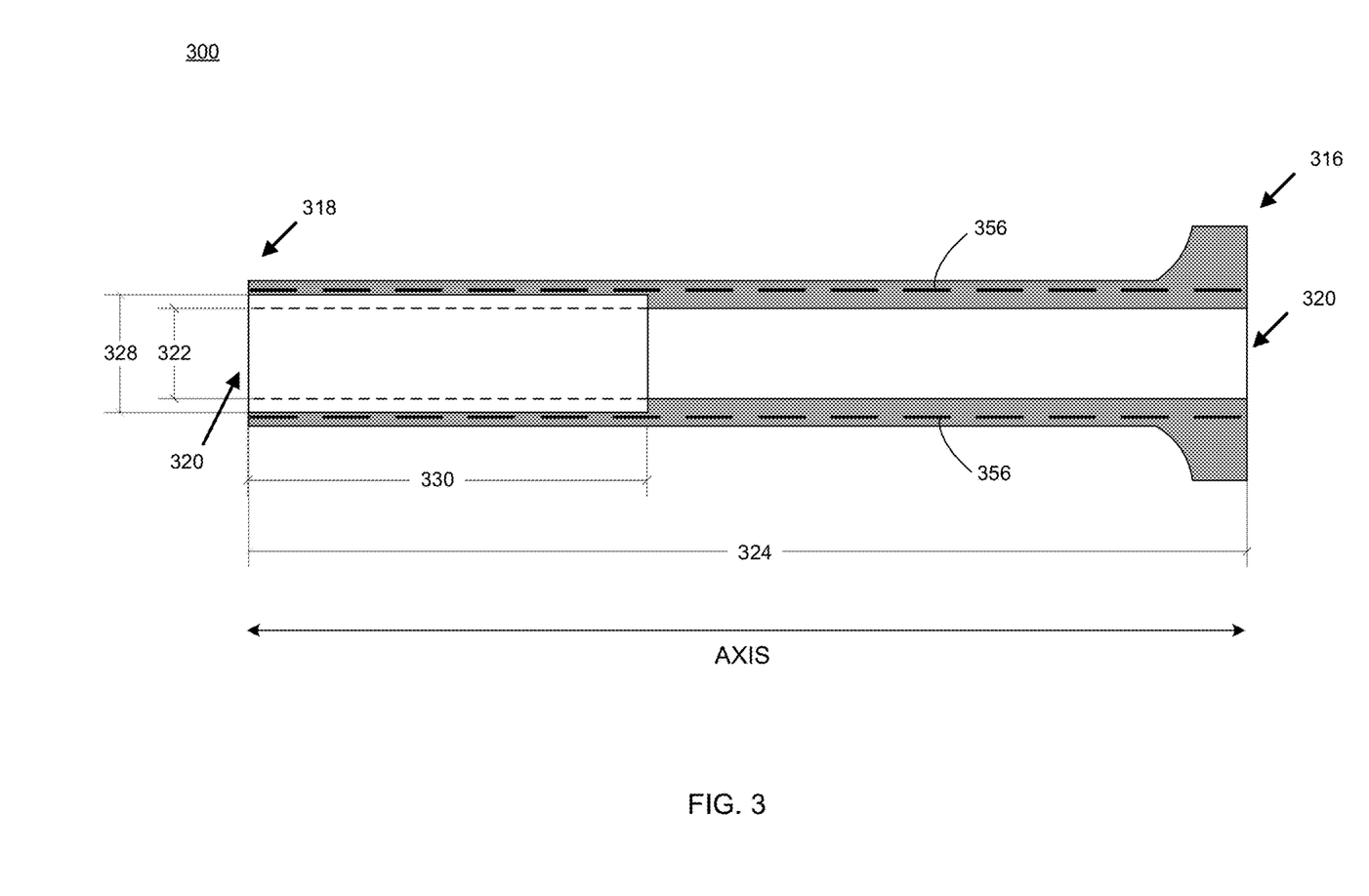
FIG. 3 is an example diagrammatic view of a dispensing apparatus housing according to one or more example implementations of the disclosure.
Figure 4A:
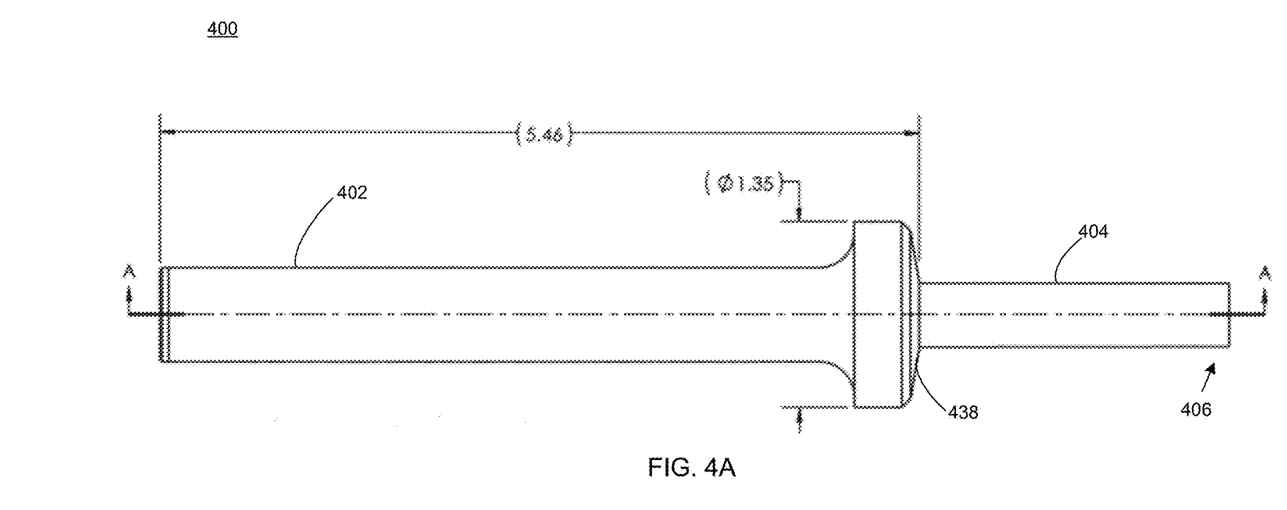
FIG. 4A is an example diagrammatic view of a dispensing apparatus according to one or more example implementations of the disclosure.
Figure 4B:
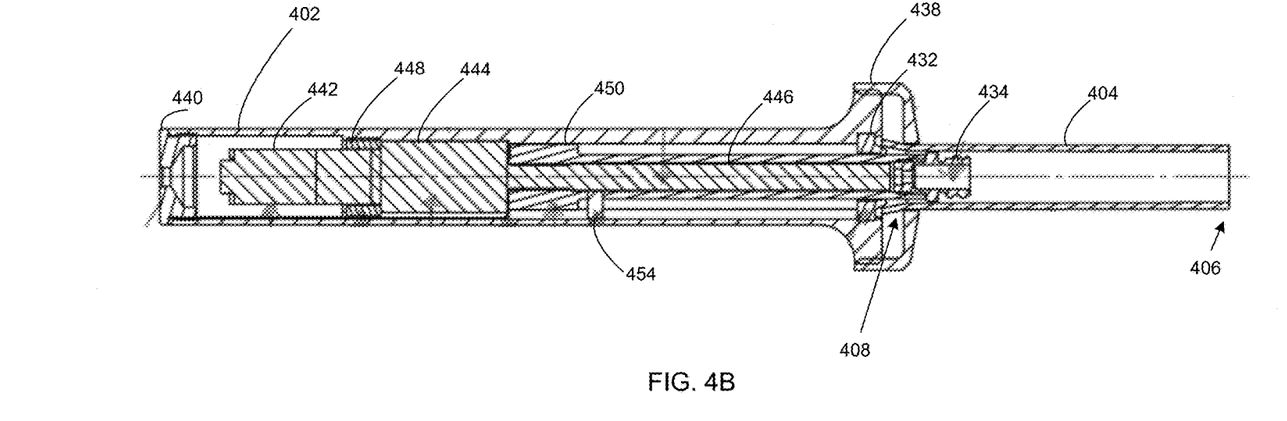
FIG. 4B is an example diagrammatic view of a dispensing apparatus according to one or more example implementations of the disclosure.

For example, and referring also to at least to FIGS. 1-6, an example dispensing apparatus 100 is shown. It will be appreciated that the example dimensions shown in FIGS. 4A-4B may vary without departing from the scope of the disclosure. In some embodiments, the dispensing apparatus 100 (e.g., pencil gun) may include a housing 102 (e.g., a gun shell). Referring also to FIG. 3, the housing 302 may define a hollow body including a first end 316 and a second end 318. The length of the housing from the first end 316 to the second end 318 may define an axis (e.g., an example axis is labeled "AXIS" in FIG. 3). The hollow body of the housing 302 may include one or more hollow portions. A first hollow portion 320 with a first width 322 may extend along the axis for a first length 324. In one example, the first length 324 may extend through the entire housing from the first end 316 to the second end 318. A second hollow portion 326 with a second width 328 may extend from the second end 318 of the housing along the axis for a second length 330. The combination of the first 320 and second hollow portions 326 may define a "counterbore" or "countersink" within housing 302. In some embodiments, housing 302 of dispensing apparatus 300 may be made of metal, including at least anodized aluminum. In one example, housing 302 may be made of anodized 2011 aluminum.

As will be discussed in greater detail below and referring also to FIG. 2, one or more of the following may be disposed within and/or on the housing 202: a motor assembly 212, a drive tube assembly 214, a wiper 232, a piston hub 234, a membrane switch 236, a retainer ring 138, and an endcap 240. In some embodiments, a drive tube assembly 214 may be received into the first hollow portion 320 of housing 202. The drive tube assembly 214 may be oriented within the first hollow portion 320 along the axis of housing 202. In some embodiments, the first end 316 of housing 302 may include an opening. In one example, the opening may be the first hollow portion 320. As will discussed in greater detail below, at least a portion of the drive tube assembly 214 may be configured to pass through (e.g., extend from and retract into) housing 202 through the opening 320. In some embodiments, the first end 316 of the housing 202 may include a wiper 232 over and/or within the opening 320. In one example, the wiper 232 may be configured to receive at least a portion of the drive tube assembly 214 such that at least a portion of the drive tube assembly 214 may pass through (e.g., extend from and retract into) opening 320 of the first end 316 of housing 202 through wiper 232.

In some embodiments, motor assembly 212 may be oriented within housing 202 along the axis defined between the first 316 and second ends 318 of housing 302. Motor assembly 212 may be received into second hollow portion 326 within housing 302. In one example, a portion of the motor assembly 212 may rest against the lip or edge formed between the first 320 and second hollow portions 326. As will be discussed in greater detail below, the drive tube assembly 214 may be configured to receive at least a portion of the motor assembly 212. In some embodiments, an end cap 240 may be received within the second hollow portion 326 of housing 302. End cap 240 may include a flange configured to engage with the edge of housing 202.

In some implementations, motor assembly 212 may be configured to interact with a syringe 104 to dispense fluid from dispensing apparatus 100. Motor assembly 212 may be encased within the housing 202 of dispensing apparatus 200. In some embodiments, motor assembly 212 may include one or more of: a motor 142; a leadscrew 144; and a thrust coupling 146.

Motor assembly 212 may be anchored (e.g., secured in place) within the housing 202 of dispensing apparatus 200. In one example, motor assembly 212 may be stationary within the housing 202 (e.g., secured from moving within housing 202). For example, motor assembly 212 may be anchored to housing 202 via motor locking nut 248. In some embodiments, motor assembly 212 may be configured to be coupled to the motor locking nut 248. The coupling may include a threaded coupling, a tapered coupling, a friction coupling, a snap-in coupling, an adhesive bonding, and similar known mechanisms and combinations thereof. In some embodiments, motor locking nut 248 may be made of metal. In one example, motor locking nut 248 may be made of brass. Motor locking nut 248 may be configured to be coupled to at least a portion of motor assembly 212 and may be attached to housing 202 of dispensing apparatus 200. The attachment of motor locking nut 248 to housing 202 of dispensing apparatus 200 may include a threaded coupling, a tapered coupling, a friction coupling, a snap-in coupling, an adhesive bonding, and similar known mechanisms and combinations thereof. In some embodiments, motor assembly 212 may include a motor 142. In one example, motor 142 may be a stepper motor. Motor 142 may be configured to be coupled to leadscrew 144. In some embodiments and as will be discussed in greater detail below, motor 142 may be configured to be coupled to leadscrew 144 via thrust coupling 146.

In some embodiments, motor assembly 212 may include a thrust coupling 146. Thrust coupling 146 may include a gearing system capable of isolating load thrust from motor 142. In some embodiments, thrust coupling 146 may be configured to couple motor 142 to leadscrew 144 such that the operation of motor 142 rotates leadscrew 144 via thrust coupling 146. When a load on leadscrew 144 exceeds a predefined threshold, thrust coupling 146 may isolate motor 142 from the load on leadscrew 144. In one example, thrust coupling 146 may be stationary within the housing 202 (e.g., secured from moving within housing 202). For example, thrust coupling 146 may be anchored to housing 202 via motor locking nut 248. In some embodiments, thrust coupling 146 may be configured to be coupled to the motor locking nut 248. The coupling may include a threaded coupling, a tapered coupling, a friction coupling, a snap-in coupling, an adhesive bonding, and similar known mechanisms and combinations thereof. In some embodiments, thrust coupling 146 may be made of metal. In one example, thrust coupling 146 may be made of brass. Thrust coupling 146 may be configured to be coupled to at least a portion of motor assembly 212 and may be attached to housing 202 of dispensing apparatus 200.

In some embodiments, motor assembly 212 may include leadscrew 144. In one example, motor 142 may be configured to engage leadscrew 144. Leadscrew 144 may be coupled to motor 142 and extend from motor 142 along the axis between the first 316 and second ends 318 of housing 300 toward the first end 316 of the housing. Operation of motor 142 may generate and/or cause rotation of leadscrew 144. Leadscrew 144 may rotate in response to the operation of motor 142. As will be discussed in greater detail below, rotation of leadscrew 144 may maneuver drive tube assembly 214. In one example, leadscrew 144 may be a threaded rod, from which drive tube assembly 214 may slide down and up as a nut (or similar) rotates respectively via motor 142. In some embodiments, leadscrew 144 may be fixed and/or may not move through motor 142. As will discussed in greater detail below, leadscrew 144 may be partially and/or completely encased in housing 102 of dispensing apparatus 100.

In some embodiments, dispensing apparatus 100 may include a drive tube assembly 214. Drive tube assembly 214 may include one or more of a drive tube 150 and a leadscrew nut 152. Drive tube 150 may be a rod or a hollow tube. In one example, drive tube 150 may be hollow and may be configured to partially and/or completely encase leadscrew 144. Partially and/or completely encasing leadscrew 144 may protect the leadscrew and/or other components of the drive tube assembly 214 and the motor assembly 212 from the contents of syringe 104 and/or potential contaminants. In some embodiments, drive tube 150 may be configured to engage leadscrew 144 with a fixed leadscrew nut 152. In some implementations, operations of the above-noted motor 142 may cause leadscrew nut 152 to move in a forward (e.g., toward the first end of the housing) or reverse direction (e.g., toward the second end of the housing), drive tube assembly 214 may similarly move. In other words, leadscrew 144 may rotate with the operation of motor 142 which may extend and/or retract drive tube assembly 214 in relation to the first end 116 of housing 102. In some embodiments, drive tube assembly 214 may be made of metal. In one example, drive tube assembly 214 may be made of nickel plated brass. In some embodiments, one or more of the components of the drive tube assembly 214 (e.g., drive tube 150 and/or leadscrew nut 152) may be made of metal. In one example, drive tube 150 and/or leadscrew nut 152 may be made of nickel plated brass.

In some embodiments, one or more of the motor assembly 212 and the drive tube assembly 214 may be rotationally fixed to housing 202. "Rotationally fixed" as used herein may include, but is not limited to, fixing an object from rotating in relation to another object. For example, one or more of the motor assembly 212 and the drive tube assembly 214 may be rotationally fixed to housing 202 such that motor assembly 212 and/or the drive tube assembly 214 may not rotate relative to housing 202. This may include rotating about housing 202 and/or within housing 202. In some embodiments, each of the motor assembly 212 and/or driver tube assembly 214 may be equipped with an anti-rotation device 154 which may prevent the motor assembly 212 and/or the driver tube assembly 214 from rotating while extending and retracting in both forward (e.g., toward the first end 316 of housing 302) or reverse directions (e.g., toward the second end 318 of housing 302). In one example, anti-rotational device 154 may include one or more anti-rotational pins 154. For instance, and as shown in FIG. 1, one or more of the motor assembly 212 and/or components of motor assembly 212 (e.g., motor 142 and thrust coupling 146) and driver tube assembly 214 and/or components of driver tube assembly 214 (e.g., drive tube 150 and leadscrew nut 152) may be rotationally fixed within housing 102. In one example, each of motor 142 and driver tube 150 may be rotationally fixed with one or more rotational pins 154 (e.g., anti-rotational devices). In one example, the one or more rotational pins 154 may be attached to the motor 142, as well as other components of motor assembly 212, and/or the driver tube 150, as well as other components of driver tube assembly 214. The one or more anti-rotational pins 154 may extend perpendicularly from motor 142 and/or the driver tube 150. In some embodiments, the anti-rotational pins 154 may interact with interior wall of housing 100. For example, the one or more anti-rotational pins 154 may press against the interior wall of housing 100 to prevent rotation by virtue of friction between the pin(s) 154 and the housing wall. In some embodiments, the one or more anti-rotational pins 154 may engage with one or more slots, holes, or other engagement mechanisms within the housing (e.g., anti-rotational slots 156). In some embodiments, as the drive tube 150 extends from and retracts into dispensing apparatus 100, the rotational movement of leadscrew 144 may cause the drive tube 150 and/or drive tube assembly 214 to similarly rotate. To prevent rotation, the one or more anti-rotational pins 154 may engage with the one or more slots, holes, surface features, or other engagement mechanisms within the housing (e.g., anti-rotational slots 156) to prevent the rotational movement of drive tube 150 and/or drive tube assembly 214. In some embodiments, housing 102 may include a one or more slots and/or tracks (not shown) extending along the axis, between the first 316 and second ends 318 of the housing, into which the anti-rotational pins 152 may engage to prevent the rotation of the driver tube assembly. While the above example describes the possible rotation of the driver tube assembly 214, the motor assembly 212 may be similarly rotationally fixed to housing 100.

In some embodiments, dispensing apparatus 100 may include a piston hub 134, wherein a first end of the piston hub 134 may be configured to be coupled to a first end of the driver tube assembly 242, and/or driver tube 150, and a second end of the piston hub 134 may be configured to be coupled to piston assembly 110 of syringe 104. Piston hub 134 may be disposed at the first end of the drive tube assembly 214 (e.g., the end directed into opening 320 of the first end 316 of housing 300 and/or into piston assembly 110 of syringe 104). The piston hub 134 may include a threaded coupling, a tapered coupling, a friction coupling, a snap-in coupling, an adhesive bonding, and similar known mechanisms and combinations thereof that may operatively engage a corresponding aperture defined by piston assembly 110 of syringe 104. As such, the description of the coupling should be taken as an example only and not to limit the scope of the disclosure.

Additionally and/or alternatively, piston hub 134 may be disposed at the first end of the drive tube 150 of the drive tube assembly 214 (e.g., the end directed into opening 320 of the first end 316 of housing 300 and/or into piston assembly 110 of syringe 104). Piston hub 134 may be configured to couple drive tube assembly 214 to a piston assembly 110 of syringe 104. In some embodiments, piston hub 134 may facilitate a direct connection between drive tube assembly 214 and piston assembly 110 of syringe 104. This may allow piston assembly 110 to be precisely extended and retracted within syringe barrel 104. In some embodiments, piston hub 134 may protect drive tube assembly 214 from exposure to the contents of syringe 104. As discussed above, the movement of the drive tube assembly 214 may create positive or negative pressure within syringe 104 to dispense contents.

In some embodiments, the opening 320 in the first end 316 of housing 100 may include a wiper 132 (e.g., seal) and at least a the portion of the driver tube assembly 214 may be configured to extend from and retract into an opening 320 in the first end 316 of housing 100 through wiper 132. In some embodiments, wiper 132 may fit firmly around drive tube assembly 214. In one example, wiper 132 may form a ring-like shape through which at least a portion of driver tube assembly 214 may pass. In some embodiments, the outside edge of the wiper 132 may be fixed to the interior edge of the opening 320 in the first end 316 of housing 100. Wiper 132 may act as a wiper/seal as drive tube assembly 214 extends and retracts through wiper 132. Wiper 132 may create a liquid tight sealed chamber which may prevent fluids and debris from entering housing 100. Wiper 132 may protect the motor 142, thrust coupling 146, and leadscrew 144 (e.g., motor assembly 212) from exposure to potential spills or other contaminants. In one embodiment, wiper 132 may be made of PTFE (Teflon) which may provide a high slip/no stick surface that may allow the drive tube 150 to slide freely through wiper 132. In addition, a wiper 132 formed of PTFE may prevent drive tube assembly 214 from becoming bonded to wiper 132. Wiper 132 may be easily cleanable, and may be suitable for use with adhesives, liquids, gels, etc. In one example, wiper 132 may be suitable for use with cyanoacrylate (i.e., CA or super glue).

In some embodiments and as shown in FIG. 2, dispensing apparatus 200 may include a membrane switch 236 wherein membrane switch 236 may be configured to activate when the portion of the driver tube assembly 214 is fully retracted into housing 200. Membrane switch 236 may include a ring-like structure disposed to receive a portion of the motor assembly 212. In some embodiments, leadscrew 144 of motor assembly 212 may pass through membrane switch 236. In some embodiments, membrane switch 236 may be disposed between the thrust coupler 146 of the motor assembly 212 and the driver tube assembly 214. Membrane switch 236 may be configured to make physical contact with the drive tube assembly 214 when the drive tube assembly 214 is fully retracted within the housing. The drive tube may include a pin that protrudes from the back of the drive tube. This pin, which may be a part of the drive tube, may come into contact with the membrane switch when fully retracted causing the switch to be activated. In some embodiments, physical contact with the drive tube assembly 214 may alter an electromagnetic signal transmitted through the structure of the membrane switch 236. In addition, proximity of the drive tube assembly 214 may interfere with and/or change a voltage, amperage, resistance, and/or conductivity associated with membrane switch 236. In one example, contact with the drive tube assembly 214 may cause membrane switch 236 to transmit a signal (e.g., membrane switch signal). In some embodiments, the membrane switch signal may represent a change in a constant signal applied to the membrane switch 236, wherein contact with the driver tube assembly 214 disrupts the constant signal. In this example, disruption may constitute the membrane switch signal.

In some embodiments, the membrane switch signal may be transmitted through a wired connection via wires connected to the membrane switch 236. In one example, the membrane switch signal may be transmitted wirelessly. In some embodiments, the transmission of the signal and/or disruption in an constant signal from the membrane switch 236 may indicate that the drive tube assembly 242 is fully retracted. In some embodiments, activation of the membrane switch 236 may provide a repeatable and accurate "home" position.

In some embodiments and as discussed above, dispensing apparatus 200 may include an end cap 240. In some embodiments, end cap 240 may be received within the second hollow portion 326 of housing 300. End cap 240 may include a flange configured to engage with the edge of housing 300. In some embodiments, end cap 240 may be made of metal, including at least anodized aluminum. In one example, end cap 240 may be made of anodized 2011 aluminum. In some embodiments, end cap 240 may create a liquid tight seal at the second end 318 of dispensing apparatus 300 and may facilitate the entry of an electrical cable 258.

Figure 5:
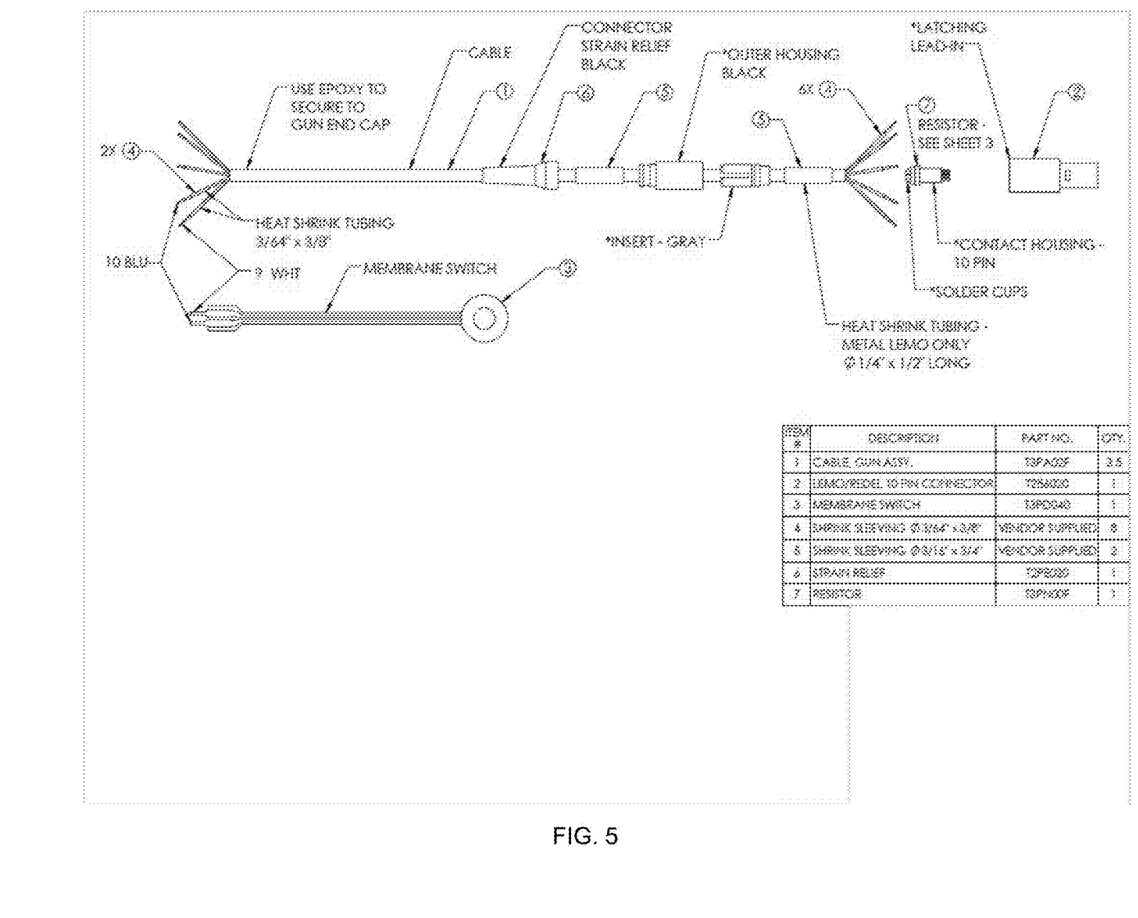
FIGS. 5-6 are example diagrammatic views of electrical cable and/or components associated with the dispensing apparatus according to one or more example implementations of the disclosure.
Figure 6:
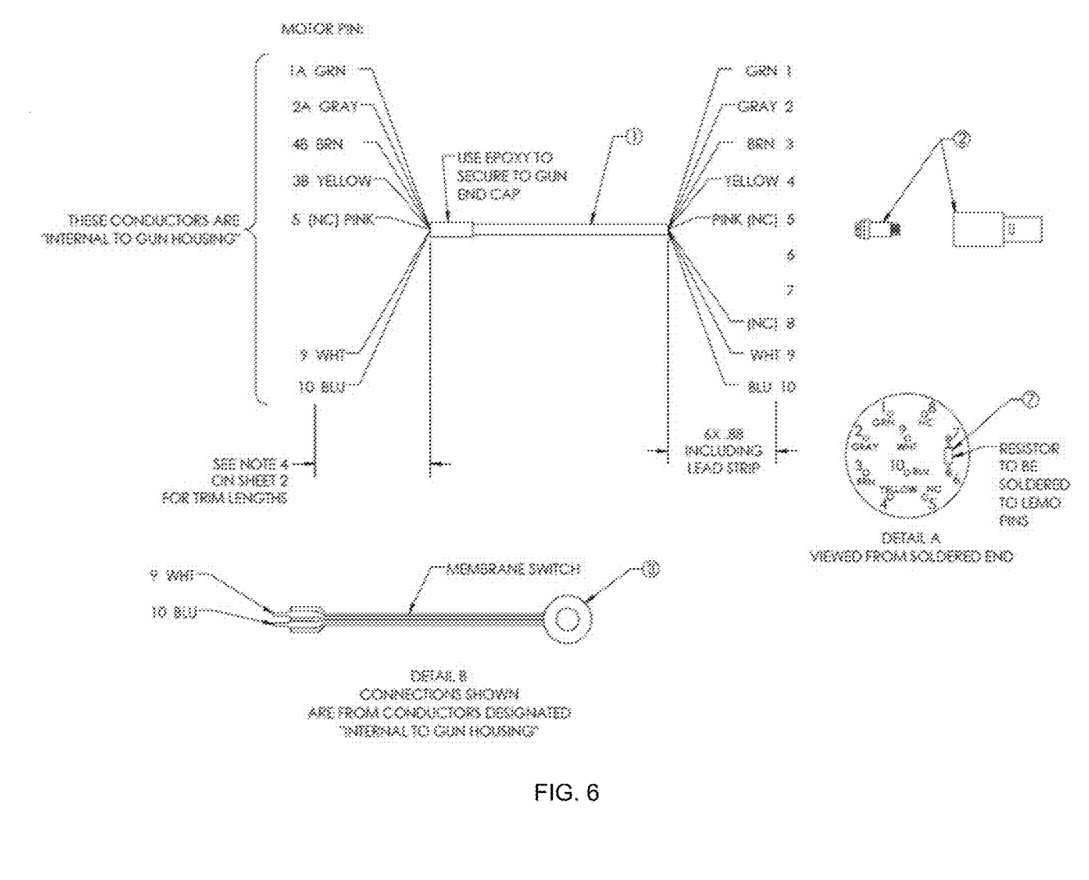

Referring also to FIGS. 5 and 6, electrical cable 258 may include one or more conductors (e.g., wires) for communication with and operation of dispensing apparatus 100. Electrical cable 258 may include one or more conductors for communication with and operation of membrane switch 236. For example, the method of making the dispensing apparatus may include, but is not limited to, stripping e.g., 0.6 inches of a black cable outer jacket on the lemo end and e.g., 1.75 inches on the gun end. Conductors may be separated from metal shielding and the shielding may be cut flush to the cable outer jacket. A clear plastic covering may be removed. As shown in FIG. 6, the pink conductor may be cut e.g., 0.25 inches maximum from the jacket and left unstripped and unterminated on both ends. The individual conductors on the lemo end may be trimmed to lengths shown in FIG. 6. However, it will be appreciated that other lengths are within the scope of the presented disclosure. Individual conductors designated as "INTERNAL TO GUN HOUSING" as shown in FIG. 6 may be trimmed as follows: a brown conductor (e.g., "BRN" as shown in FIG. 6), a yellow conductor, a green conductor (e.g., "GRN" as shown in FIG. 6), a blue conductor (e.g., "BLU" as shown in FIG. 6), a gray conductor, and a white conductor (e.g., "WHT" as shown in FIG. 6) may be trimmed. Both ends of each conductor may be stripped (except the pink conductor) with e.g., ⅛ inch being stripped on the gun end. The conductors may be twisted and tinned. All conductors to be terminated may be soldered as shown in "DETAIL A" of FIG. 6. Conductors 9 and 10 may be soldered to the membrane switch as follows: the bare tinned wires may be soldered to the tabs of the membrane switch; the connections may be shrink-wrapped; a soldering iron (not shown) may be set to e.g., 450° F.; and conductors 9 and 10 may maintain contact to soldering tab for e.g., 3-5 seconds. All connections may be encased in shrink tube before soldering. In some implementations, standard IPC-610 may be used for all soldering connections and the assembly may be RoHS compliant (e.g., Restriction of Hazard Substances Directive).

In some embodiments, dispensing apparatus 100 may include a retainer ring 160, wherein the retainer ring 160 may be configured to receive a non-dispensing end 106 of the syringe and may be further configured to be coupled to the first end 316 of housing 300. As described above, a syringe 104 may define a cylinder with a first end 106 and a second end 106, a piston assembly, an output at the first end of the cylinder 106 (e.g., the "dispensing end") and an opening for a shaft at the second end of the cylinder 108 (e.g., the "non-dispensing end"). In some embodiments, the non-dispensing end 108 of syringe 104 may include a flange (not shown). Additionally and/or alternatively, the cylinder may taper from non-dispensing end 106 to dispensing end 104 such that the diameter of the non-dispensing end is greater than the diameter of the dispensing end.

In some embodiments and referring again to FIG. 1, retainer ring 160 may define a ring-like structure with a first aperture 462 and a second aperture 464. The first aperture 462 of retainer ring 160 may be configured to receive the first end 316 of housing 102 of dispensing apparatus 100. The retainer ring 160, at least the first aperture 462, may be configured to couple to the first end 316 of housing 102. In some embodiments, the coupling between the retainer ring 160 and the first end 316 of the housing 102 may include a threaded coupling, a tapered coupling, a friction coupling, a snap-in coupling, an adhesive bonding, and similar known mechanisms and combinations thereof. The second aperture 462 may be configured to receive a non-dispensing end 106 of syringe 104. In some embodiments, the retaining ring 160 may be configured to couple to the non-dispensing end 108 of the syringe 104. The coupling between the retainer ring 160 and the non-dispensing end 108 of the syringe 104 may include a threaded coupling, a tapered coupling, a friction coupling, a snap-in coupling, an adhesive bonding, and similar known mechanisms and combinations thereof.

For example and as described above where a non-dispensing end 108 of a syringe 104 includes a flange (not shown), the cylinder of the syringe may pass through the second aperture 464 while the flange rests against the lip formed by second aperture 464. Additionally and/or alternatively where the diameter of cylinder of the syringe tapers along the length of the syringe, the diameter of the second aperture 464 of the retaining ring 160 may be greater than the diameter of the dispensing end 106 of syringe 104 but less than the diameter of the non-dispensing end 108 of syringe 104. In some embodiments, dispensing apparatus 100 may be used with both 3 cc and 5 cc syringes. While 3 cc and 5 cc syringes are described, other syringes of various volumes may be used as well. In some embodiments, retaining ring 160 may be made of metal. In one example, retaining ring 160 may be made of anodized aluminum. In another example, retaining ring 160 may be made of anodized 2011 aluminum. In one example, retaining ring 160 may facilitate the installation of either a 3 cc or 5 cc syringe to dispensing apparatus 100. The retaining ring 160 may, for example, thread onto the first end 316 of the housing 102 firmly holding syringe 104 in place while the piston assembly 110 extends and retracts within syringe 104 While a threaded coupling has been described, any suitable coupling for securing the retaining ring to the first end of the dispenser is within the scope of the present disclosure.

In some implementations, syringe 104 may define a volume that contains a fluid, such as an adhesive; however, it will be appreciated that other fluids may be used as well. For example, syringe 104 may be configured as a 3 cc or a 5 cc container; however, it will be appreciated that other volumes may be used as well. In some implementations, syringe 104 may be configured as a single-use fluid source. For example, during operation, dispensing apparatus 100 may dispense fluid contained by syringe 104 to, e.g., a work piece until syringe 104 is empty. The emptied syringe 104 may then be removed from dispensing apparatus 100, where a new full syringe may be inserted in its place for continued operation.

Figure 7:
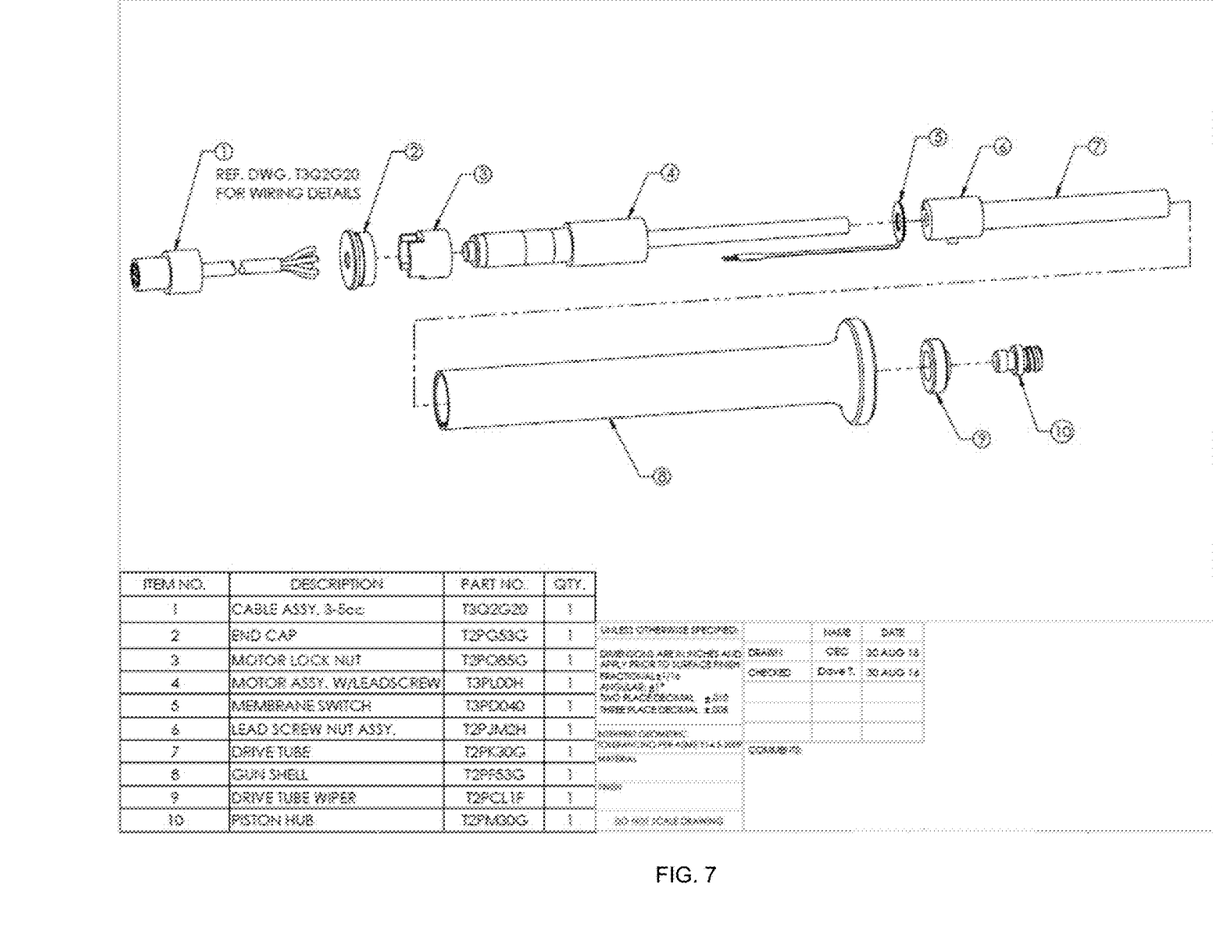
FIG. 7 is an example diagrammatic view of a dispensing apparatus housing according to one or more example implementations of the disclosure.
Figure 8:
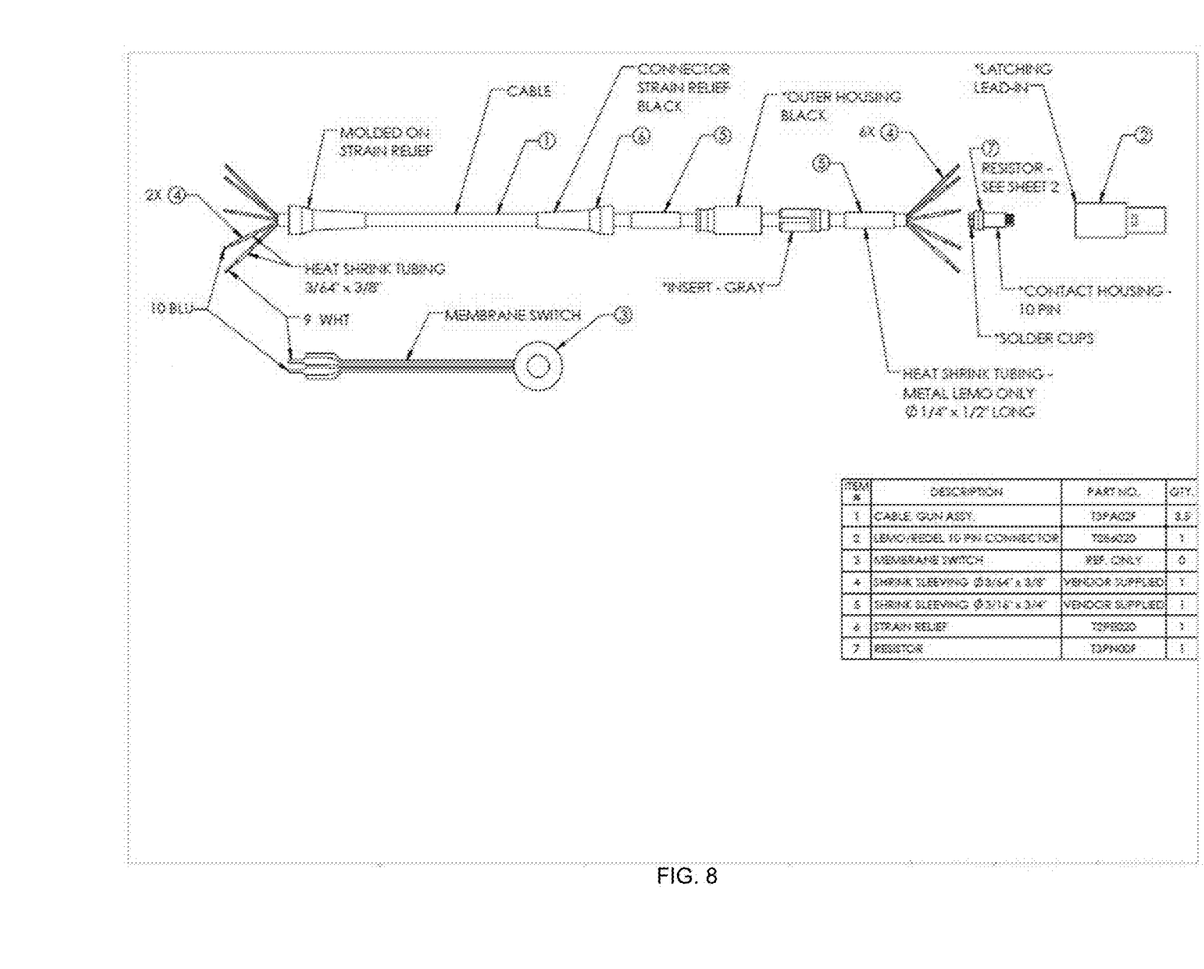
FIG. 8 is an example diagrammatic view of a dispensing apparatus according to one or more example implementations of the disclosure.
Figure 9:
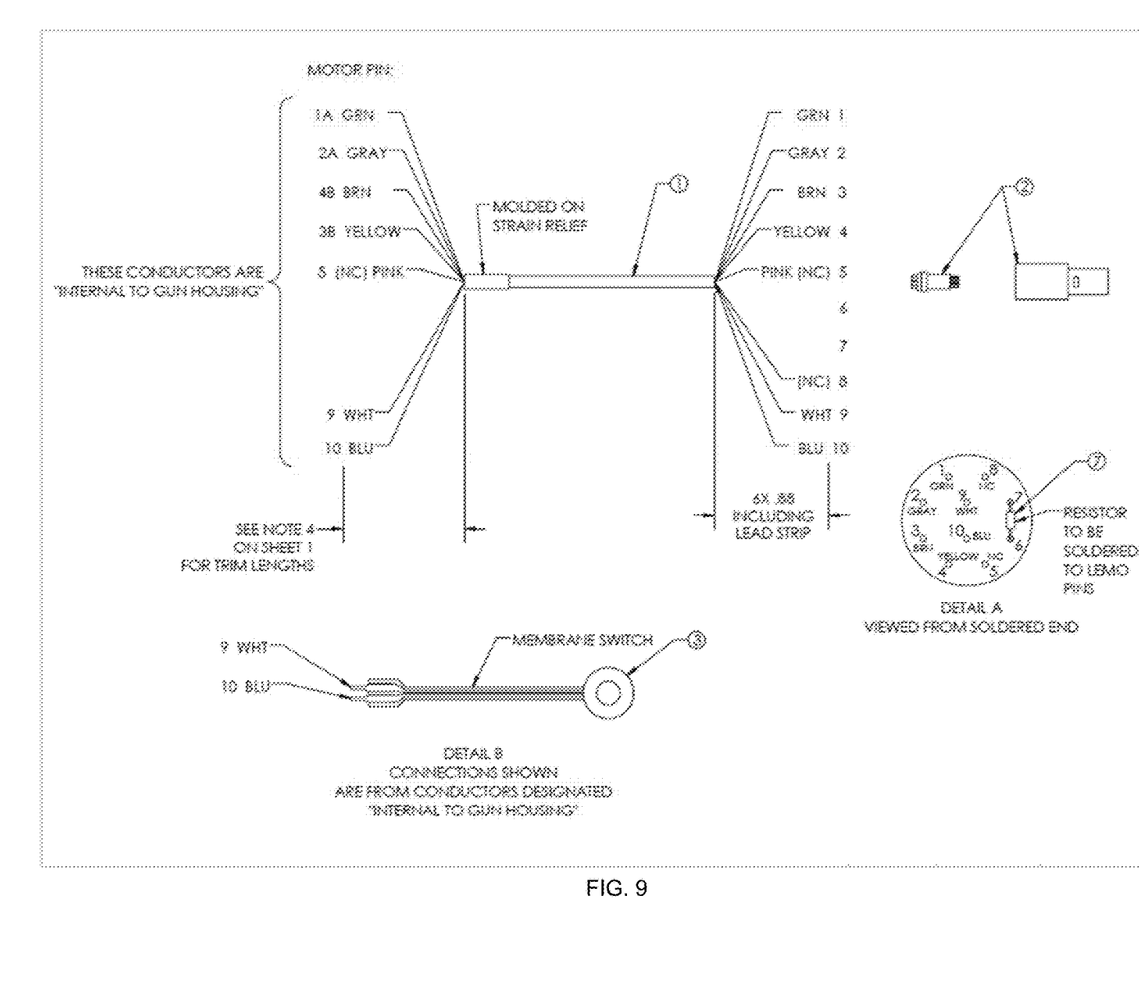
FIG. 9 is an example diagrammatic view of a dispensing apparatus according to one or more example implementations of the disclosure.

Referring also to FIGS. 7-9, additional embodiments consistent with the dispensing apparatus of the present disclosure are provided. FIG. 7 depicts a cable assembly that may be operatively connected with an end cap and motor lock unit. The motor lock unit may receive and be at least partially connect with a motor assembly having a leadscrew. One end of the motor assembly may be contained within a membrane switch and lead screw nut assembly as shown. The lead screw nut assembly may be connected with a drive tube. In some embodiments these may be separate components that are attached to one another. Alternatively, these may be one singular component. A gun shell is provided and may protect the previously described components by acting as an exterior casing. A drive tube wiper and piston hub may be operatively with portions of the drive tube, lead screw nut assembly, and/or gun shell.

Referring also to FIG. 8, another embodiment consistent with the dispensing apparatus of the present disclosure is provided. This particular embodiment shows an exploded view of an example dispensing apparatus as well as a method of making the same. FIG. 8 included a number of operations that may be used in the construction of a dispensing apparatus. For example, the method of making the dispensing apparatus may include, but is not limited to, stripping e.g., 0.6 inches of a black cable outer jacket on the lemo end and e.g., 1.75 inches on the gun end. Conductors may be separated from metal shielding and the shielding may be cut flush to the cable outer jacket. A clear plastic covering may be removed. As shown in FIG. 9, the pink conductor may be cut e.g., 0.25 inches maximum from the jacket and left unstripped and unterminated on both ends. The individual conductors on the lemo end may be trimmed to lengths shown in FIG. 9. However, it will be appreciated that other lengths are within the scope of the presented disclosure. Individual conductors designated as "INTERNAL TO GUN HOUSING" as shown in FIG. 9 may be trimmed as follows: a brown conductor (e.g., "BRN" as shown in FIG. 9), a yellow conductor, a green conductor (e.g., "GRN" as shown in FIG. 9), a blue conductor (e.g., "BLU" as shown in FIG. 9), a gray conductor, and a white conductor (e.g., "WHT" as shown in FIG. 9) may be trimmed to a length of e.g., 1.75 inches. Both ends of each conductor may be stripped (except the pink conductor) with e.g., ⅛ inch being stripped on the gun end. The conductors may be twisted and tinned. All conductors to be terminated may be soldered as shown in "DETAIL A" of FIG. 9. Conductors 9 and 10 may be soldered to the membrane switch as follows: the bare tinned wires may be soldered to the tabs of the membrane switch; the connections may be shrink-wrapped; a soldering iron (not shown) may be set to e.g., 450° F.; and conductors 9 and 10 may maintain contact to soldering tab for e.g., 3-5 seconds. All connections may be encased in shrink tube before soldering. In some implementations, standard IPC-610 may be used for all soldering connections and the assembly may be RoHS compliant (e.g., Restriction of Hazard Substances Directive). FIGS. 8-9 depict examples showing a molded on strain relief component. Again, these figures are provided merely by way of example. Numerous other operations may also be used in the construction of a dispensing apparatus.

It should be noted that some of the description and figures included herein discuss various sizes, dimensions, and quantities. These are provided merely by way of example as possible ways in which the embodiments of the present disclosure may be implemented. The present disclosure is not meant to be limited to these numbers.

The terminology used herein is for the purpose of describing particular implementations only and is not intended to be limiting of the disclosure. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps (not necessarily in a particular order), operations, elements, and/or components, but do not preclude the presence or addition of one or more other features, integers, steps (not necessarily in a particular order), operations, elements, components, and/or groups thereof.

The corresponding structures, materials, acts, and equivalents (e.g., of all means or step plus function elements) that may be in the claims below are intended to include any structure, material, or act for performing the function in combination with other claimed elements as specifically claimed. The description of the present disclosure has been presented for purposes of illustration and description, but is not intended to be exhaustive or limited to the disclosure in the form disclosed. Many modifications, variations, substitutions, and any combinations thereof will be apparent to those of ordinary skill in the art without departing from the scope and spirit of the disclosure. The implementation(s) were chosen and described in order to explain the principles of the disclosure and the practical application, and to enable others of ordinary skill in the art to understand the disclosure for various implementation(s) with various modifications and/or any combinations of implementation(s) as are suited to the particular use contemplated.

Having thus described the disclosure of the present application in detail and by reference to implementation(s) thereof, it will be apparent that modifications, variations, and any combinations of implementation(s) (including any modifications, variations, substitutions, and combinations thereof) are possible without departing from the scope of the disclosure defined in the appended claims.

What is claimed is:

1. An apparatus, comprising:
    a housing, wherein the housing includes a first end and a motor, wherein the first end is configured to be coupled to a syringe;
    wherein the motor is configured to be operatively connected to a drive tube, wherein at least a portion of the drive tube is configured to extend from and retract into an opening in the first end of the housing in response to the motor;
    wherein the drive tube is rotationally fixed to the housing; and
    wherein a first end of the drive tube is configured to be coupled to a piston of the syringe.

2. The apparatus of claim 1, wherein the opening of the first end of the housing includes a wiper and the portion of the driver tube is further configured to extend from and retract into the first end of the housing through the wiper.

3. The apparatus of claim 1, further comprising a piston hub, wherein a first end of the piston hub is configured to be coupled to the first end of the driver tube and a second end of the piston hub is configured to be coupled to a piston of the syringe.

4. The apparatus of claim 1, further comprising a retainer ring, wherein the retainer ring is configured to receive a non-dispensing end of the syringe and is further configured to be coupled to the first end of the housing.

5. The apparatus of claim 1, further comprising a membrane switch, wherein the membrane switch is configured to activate when the portion of the driver tube is fully retracted into the housing.

6. The apparatus of claim 1, wherein one or more of the motor and the drive tube are rotationally fixed to the housing with an anti-rotational device.

7. The apparatus of claim 1, wherein the position of the motor within the housing is fixed.

8. The apparatus of claim 1, wherein the motor includes a thrust coupling.

9. A pencil gun for use with a syringe having a cylinder with a first and second ends, a piston assembly, an output at the first end and an opening for a shaft at the second end of the cylinder, the pencil gun comprising:
    a housing, wherein the housing includes a first end and a motor, an opening for a shaft at the first end, wherein the first end is configured to be coupled to the second end of the syringe;
    wherein the motor is configured to be operatively connected to a drive tube, wherein at least a portion of the drive tube is configured to extend from and retract into the opening in first end of the housing in response to the motor;
    wherein the drive tube is rotationally fixed to the housing; and
    wherein a first end of the drive tube is configured to be coupled to the piston assembly of the syringe.

10. The pencil gun of claim 9, wherein the opening of the first end of the housing includes a wiper and the portion of the driver tube is further configured to extend from and retract into the first end of the housing through the wiper.

11. The pencil gun of claim 9, further comprising a piston hub, wherein a first end of the piston hub is configured to be coupled to the first end of the driver tube and a second end of the piston hub is configured to be coupled to a piston of the syringe.

12. The pencil gun of claim 9, further comprising a retainer ring, wherein the retainer ring is configured to receive a non-dispensing end of the syringe and is further configured to be coupled to the first end of the housing.

13. The pencil gun of claim 9, further comprising a membrane switch, wherein the membrane switch is configured to activate when the portion of the driver tube is fully retracted into the housing.

14. The pencil gun of claim 9, wherein one or more of the motor and the drive tube are rotationally fixed to the housing with an anti-rotational device.

15. The pencil gun of claim 9, wherein the position of the motor within the housing is fixed.

16. The pencil gun of claim 9, wherein the motor includes a thrust coupling.

* * * * *